United States Patent [19]

Miyanohara et al.

[11] Patent Number: 5,707,862
[45] Date of Patent: *Jan. 13, 1998

[54] SHUTTLE VECTOR

[75] Inventors: Atsushi Miyanohara, Neyagawa; Akio Toh-e, Hiroshima; Kenichi Matsubara, Osaka, all of Japan

[73] Assignees: Juridical Foundation The Chemi-Sero-Therapeutic Research Institute, Kumamoto-ken; Science and Technology Agency, Minister's Secretariat Director of Finance Division, Tokyo-to, both of Japan

[*] Notice: The portion of the term of this patent subsequent to Oct. 18, 2005, has been disclaimed.

[21] Appl. No.: 622,344

[22] Filed: Dec. 5, 1990

Related U.S. Application Data

[63] Continuation of Ser. No. 61,441, Jun. 15, 1987, which is a continuation of Ser. No. 522,668, Aug. 12, 1983, abandoned.

[30] Foreign Application Priority Data

Dec. 7, 1989 [CH] Switzerland ............... 4397/89

[51] Int. Cl.$^6$ ............... C12N 15/00; C12N 15/09
[52] U.S. Cl. ............... 435/320.1
[58] Field of Search ............... 435/172.3, 320.1, 435/255; 935/28, 37

[56] References Cited

U.S. PATENT DOCUMENTS

| | | | |
|---|---|---|---|
| 4,387,162 | 6/1983 | Aigle et al. | 435/172 |
| 4,778,761 | 10/1988 | Miyanohara et al. | 435/320 |
| 4,997,767 | 3/1991 | Nozaki et al. | 435/69.1 |

FOREIGN PATENT DOCUMENTS

| | | | |
|---|---|---|---|
| 17682 | 8/1983 | Australia | C12N 15/00 |
| 0106828 | 4/1984 | European Pat. Off. | C12N 15/00 |
| 0120551 | 10/1984 | European Pat. Off. | C12N 15/00 |
| 48082 | 3/1984 | Japan | C12N 15/00 |

OTHER PUBLICATIONS

R.A. Hitzeman, et al., Expression of a human gene for interferon in yeast, Nature, vol. 293, pp. 717–722, (1981).

B. Meyhack, et al., Two yeast acid phosphatase structural genes are the result of a tandem duplication and show different degrees of homology in their promoter and coding sequences, The Embo Journal, vol. 1, No. 6, pp. 675–680, (1982).

J. Ferguson, et al., Construction and characterization of three yeast Escherichia coli shuttle vectors designed for rapid subcloning of yeast genes on small DNA fragments, Gene, 16, pp. 191–197, (1981).

H. Rudolph, et al., The yeast PHO5 promoter: Phosphate-control elements and sequences mediating mRNA start-site selection, Proc. Natl. Acad. Sci., USA, vol. 84: 1340–44 (1987).

P. Valenzuela et al., Nature, vol. 298, pp. 347–350, (1982).

K. Arima et al., The nucleotide sequence of the yeast PHO5 gene: a putative precursor of repressible acid phosphatase contains a signal peptide, Nucleic Acids Research vol. 11(6): 1657–72 (1983).

Struhl (1981), Proc. Nat. Acad. Sci, vol. 78, pp. 4461–4465.

*Primary Examiner*—George C. Elliott
*Assistant Examiner*—Matthew Latimer
*Attorney, Agent, or Firm*—Foley & Lardner

[57] ABSTRACT

A shuttle vector containing an yeast gene and an *E. coli* gene and carrying the expression control region of acid phosphatase gene of yeast, which can be recombined with various genes under control of the phosphatase promoter, to give various recombinant plasmids. The shuttle vector is useful in genetic engineering industries.

1 Claim, 2 Drawing Sheets

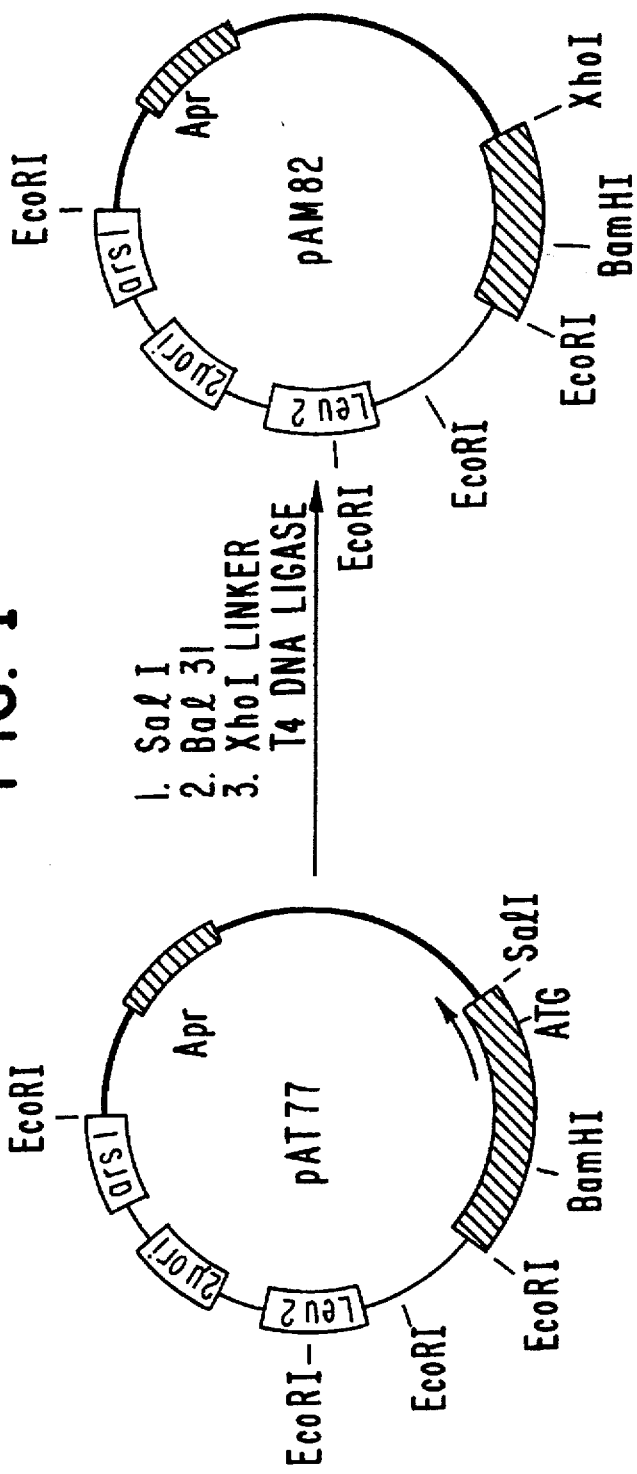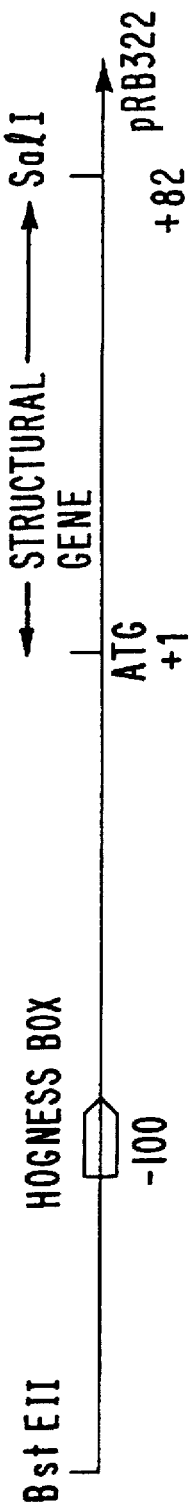
FIG. 1
FIG. 2

FIG. 3

```
                    Bst EII
                      ↓    -170         -160         -150         -140         -130
                           |            |            |            |            |
                           GTCACCTTACTTGGCAAGGCATATACCCATTTGGGATAAAGGGTAAACACTT

-120         -110         -100          -90          -80          -70          -60          -50
     |            |            |            |            |            |            |            |
    TGAATT(G)TCGAAATGAAACGTATATAAGACGCTGATGTTTGCTAAGTCGAGGTTAGTATGGCTTCATCTCTCA

-40          -30          -20          -10           +1                        +82
     |            |            |            |            |                          |
    TGAGAATAAGAACAACAAATAGAGCAAGCAAATTCGAGATTACCAATG................GTCGAC
                                                                                Sal I
```

SHUTTLE VECTOR

This application is a continuation of U.S. application Ser. No. 07/061,440 filed Jun. 15, 1987, which is a continuation of Ser. No. 06/522,668 filed Aug. 12, 1983, now abandoned.

The present invention relates to a novel shuttle vector, more particularly, relates to a shuttle vector which contains yeast gene and an *Escherichia coli* gene and carries the expression control region of the repressible acid phosphatase (said region being hereinafter referred to as "acid phosphatase promoter" or "acid phosphatase gene"), and can replicated in both *E. coli* and yeast.

With recent active studies on genetic engineering, various recombinant DNAs and transformants therefrom have been developed. In the preparation of the recombinant DNAs, a vector for inserting a specific gene is used. Such a vector includes a vector which can replicate only in a certain microorganism, e.g. in *Escherichia coli*, and a so-called shuttle vector which can replicate in two or more kinds of microorganisms, e.g. in both *E. coli* and an yeast, or in both a certain microorganism (e.g.*E. coli*) and a certain animal cell. For instance, there is very recently reported a shuttle vector which can replicate in both *E. coli* and an yeast: a vector utilizing a promoter of alcohol dehydrogenase (ADH1) which is usually used for the production of interferone with an yeast, to which promoter a gene encoding proteins of Hepatitis B virus surface antigen (hereinafter, referred to as "HBs antigen", "HBsAg" or "s antigen") is inserted [cf. Nature, 298, 347–350. (22 Jul., 1982)]. However, the shuttle vector used in this method carries an ADH1 promoter and, when a recombinant DNA inserted with HBs gene is prepared by utilizing the vector and then a transformant is prepared from the recombinant DNA, the transformant can produce the desired HBs proteins only in a small amount.

The present inventors have extensively studied on an improved *E. coli*-yeast shuttle vector which can be recombined with various genes and can express them. As a result, it has been found that a specific shuttle vector having yeast gene and *E. coli* gene and carrying the repressible acid phosphatase promoter of the yeast has desired characteristics and is useful for recombining various genes under the control of the phosphatase promoter to prepare recombinant DNAs which can give various transformed yeasts.

BRIEF DESCRIPTION OF THE DRAWINGS

FIG. 1 shows a map of plasmids pAT77 and pAM82;

FIG. 2 shows a gene map of the region around the acid phosphatase promoter of the shuttle vector pAT 77; and FIG. 3 shows the nucleotide sequence of the BstEII-Sal I region of the pAT 77 shuttle vector.

An object of the present invention is to provide a novel shuttle vector which contains *E. coli* gene and yeast gene and carries the repressible acid phosphatase promoter. Another object of the invention is to provide a shuttle vector which can be recombined with various genes under the control of the phosphatase promoter. These and other objects and advantages of the invention will be apparent to persons skilled in the art from the following description.

The shuttle vector used in the present invention is a plasmid vector which contains both of yeast gene and *E. coli* gene and carries the repressible acid phosphatase gene of the yeast. This plasmid vector can replicate in both *E. coli* and yeast, and can be used for the preparation of recombinant DNAs which are in turn used for the preparation of transformed yeasts, wherein the recombinant plasmids are prepared by using *E. coli* and then an yeast is transformed with the recombinant plasmid. The transformed yeasts thus prepared can produce the desired gene products in a large scale. In the step of the transformation of an yeast, the vector may loose the *E. coli* gene.

The yeast gene contains usually a DNA sequence which is necessary for replication of a plasmid in the yeast independently from chromosome, for instance, a DNA sequence necessary for the autonomous replication of the yeast (which is designated "ars 1"), and a DNA sequence necessary for the replication of 2 μm DNA (which is designated "2 μori"), and contains optionally a gene useful as a selective marker of the transformed yeast. The selective marker includes, for example, a leucine-producing gene, a histidine-producing gene, a tryptophane-producing gene, a uracil-producing gene, an adenine-producing gene, or the like, which may be used alone or in combination of two or more thereof.

The *E. coli* gene contains a DNA sequence necessary for the replication of the plasmid within cells of *E. coli*, for example, a DNA sequence of a replication initiating region of Col EI plasmid, and preferably contains a gene useful as a selective marker of the transformed *E. coli*. The selective marker includes, for example, an ampicillin-resistant gene, a kanamycin-resistant gene, tetracycline-resistant gene, chloramphenicol-resistant gene, or the like, which may be used alone or in combination of two or more thereof. Commonly used *E. coli* DNA is pBR322 which contains an ampicillin-resistant gene and a tetracycline-resistant gene.

The shuttle vector of the present invention is characteristic in that it carries the repressible acid phosphatase promoter of the yeast. This acid phosphatase promoter is usually a promoter of polypeptide of 60,000 dalton (P60) which constitutes the phosphatase.

Representative example of the shuttle vector is a shuttle vector which is prepared by recombining an yeast DNA containing ars 1, 2 μori and a leucine-producing gene (Leu 2) as an yeast gene with *E. coli* plasmid pBR322. The shuttle vector is designated "pAT 77" and is prepared as follows.

An EcoRI fragment of about 8,000 nucleotide pair (8 kb) containing a polypeptide (P60) gene of 60,000 dalton which constitutes the acid phosphatase (cf. PNAS, 77, 6541–6545, 1980, and PNAS, 79, 2157–2161, 1982) is inserted into the EcoRI site of known *E. coli* plasmid pBR322 (cf. Sutcliffe, J. G.; Cold Spring Harbor Symposium, 43, 77–90, 1979) to give a plasmid, which is used as the starting material. Said EcoRI fragment (8 kb DNA fragment) contains a single recognition site of a restriction enzyme Sal I at the position of dividing into about 2.8 kb and about 5.2 kb.

The starting plasmid is digested with a restriction enzyme Sal I and re-annealed with T4 DNA ligase to give a plasmid which is deficient from the Sal I site of pBR322 to the acid phosphatase gene fragment 5.2 kb (said plasmid being designated "pAT 25"). Said pAT 25 is a plasmid consisting of a fragment (about 3.7 kb) of from EcoRI site to Sal I site of pBR322 which contains the ampicillin-resistant gene and a fragment (about 2.8 kb) of from EcoRI site to Sal I site of the yeast acid phosphatase gene, wherein both fragments link at each corresponding terminal thereof.

Into the EcoRI site of the above pAT 25 is inserted an EcoRI fragment (1.4 kb) containing a DNA sequence necessary for the autonomous replication of the yeast (ars 1) and a Trp 1 gene of yeast (cf. PNAS, 76, 1035–1039, 1979) to give a plasmid (designated "pAT 26"). Said ars 1-Trp 1 fragment has a single recognition site of a restriction enzyme Hind III within the Trp 1 gene.

Into the Hind III site of the above pAT 26 is inserted a Hind III fragment containing a leucine-producing gene of yeast (Leu 2) and a DNA sequence necessary for the replication of 2 μm DNA (2 μori) (cf. Tohe, A., Guerry, p., Wichener, R. B.; J. Bacteriol., 141, 413–416, 1980) to give the desired shuttle vector pAT 77.

The pAT 77 and pAM 82 derived therefrom as described hereinafter have the structures as shown in the accompanying FIG. 1. In FIG. 1, the thick line region is the gene originated from E. coli plasmid pBR322 and the reminder region is the gene of yeast. That is, the pAT 77 contains a fragment of from EcoRI site to Sal I site containing ampicillin-resistant gene ($Ap^r$) of pBR 322 as the E. coli gene and a fragment of from EcoRI site linked with pBR 322 to Sal I site through ars 1, 2 μori, Leu 2 and the acid phosphatase gene in this order, wherein the E. coli gene and the yeast gene link at EcoRI site and Sal I site. This pAT 77 can replicate in E. coli cells because of presence of pBR322 gene and can also replicate in yeast because of presence of ars 1 and 2 μori genes. Moreover, this plasmid contains as the selective marker for transformant an ampicillin-resistant gene ($Ap^r$) at the side of E. coli and a leucine-producing gene (Leu 2) at the side of yeast, and hence, has satisfactory properties as a shuttle vector.

The gene map around the acid phosphatase promoter of the shuttle vector pAT 77 is shown in the accompanying FIG. 2. The nucleotide sequence of BstEII-Sal I region in this shuttle vector has been determined by the present inventors and is as shown in the accompanying FIG. 3. The ATG codon (methionine) shown in FIGS. 2 and 3 is the initiator codon of the acid phosphatase. That is, the repressible acid phosphatase gene fragment (about 2.8 kb) of this vector contains the region of from about 2.7 kb upstream from the structural gene to 82th nucleotide pair (82 bp) of the structural gene.

The shuttle vector pAT 77 is cleaved by treating with a restriction enzyme Sal I, followed by treating with an exonuclease BAL 31, by which a part or whole of the structural gene of acid phosphatase as shown in FIGS. 2 and 3 and further optionally various regions upstream therefrom are deleted. This deletion is effected for appropriate regions before the acid phosphatase promoter region: TATATAA (hogness box), i.e. −100 bp. The regions to be deleted can be controlled by the conditions for treating with the exonuclease and are usually in the range of from +1 to −100 bp, preferably from +1 to −50 bp. When the deletion is effected too wide range of upstream, i.e. over −100 bp, it becomes to be difficult to control of the acid phosphatase promoter, which results in lowering of yield of the desired gene products in the culture of the transformed yeast cells. On the other hand, when the deletion is insufficiently effected so that a part of the acid phosphatase structural gene is remained, there is disadvantageously produced a fusion protein of a foreign gene product and a phosphatase peptide.

After deleting a part or whole of the acid phosphatase structural gene and optionally some regions upstream therefrom, a synthetic or natural linker, for example Sal I linker or Xho I linker, is recombined thereto to give a circular plasmid, by which there is obtained a shuttle vector which can express an alien gene in the pure form under the control of the acid phosphatase promoter. This shuttle vector can readily be cleaved at the site to be recombined by treating with a conventional restriction enzyme, such as Sal I or Xho I, and hence, is preferably used in order to recombine with the desired gene.

The shuttle vector of the present invention can be used for the preparation of various recombinant plasmids by recombining it with various genes at downstream of the acid phosphatase promoter and further the preparation of various transformed yeast by the recombinant plasmids, and hence, is very useful in the field of genetic engineering industries. For instance, the shuttle vector of the present invention is used for the preparation of a recombinant plasmid inserted with an HBs gene and further the preparation of a transformed yeast therefrom which can produce HBs antigen in a large scale, said HBs antigen being the same as a natural HBs antigen obtained from human blood plasma in terms of immunological properties and hence being useful for the preparation of Hepatitis B virus vaccine.

The present invention is illustrated by the following Example and Preparation.

EXAMPLE

Preparation of shuttle vectors pAM 81, 82, 83 and 84

An EcoRI fragment of about 8,000 nucleotide pair (8 kb) containing a polypeptide (P60) gene of 60,000 dalton which constitutes the repressible acid phosphatase (available from Yeast S288C gene bank, Clarke, L. and Carbon, J., Cell, 9, 91–99, 1976) is inserted into the EcoRI site of known E. coli plasmid pBR322 to give a plasmid, which is used as the starting material.

The starting plasmid is digested with a restriction exzyme Sal I and re-annealed with T4 DNA ligase to give a plasmid pAT25 which is deficient from the Sal I site to the acid phosphatase gene fragment 5.2 kb [said plasmid pAT 25 being a plasmid consisting of a fragment (about 3.7 kb) of from EcoRI site to Sal I site of pBR322 which contains the ampicillin-resistant gene and a fragment (about 2.8 kb) of from EcoRI site to Sal I site of the yeast acid phosphatase gene, wherein both fragments link at each corresponding terminal thereof].

Into the EcoRI site of the above pAT 25 is inserted an EcoRI fragment (1.4 kb) containing ars 1 and Trp 1 gene which is prepared by treating a plasmid YRP 7 (cf. Struhl, K. et al, Proc. Natl. Acad. Sci. U.S.A., 76, 1035–1039, 1979) with EcoRI to give a plasmid pAT 26. Said ars 1-Trp 1 fragment has a single recognition site of a restriction enzyme Hind III within the Trp 1 gene.

Into the Hind III site of the above pAT 26 is inserted a Hind III fragment containing a Leu 2 and 2 μori which is prepared by treating a plasmid pSLE 1 (cf. Tohe, A. et al, J. Bacteriol., 141, 413–416, 1980) with Hind III to give the desired shuttle vector pAT 77. The pAT 77 carried on Saccharomyces cerevisiae (i.e. Saccharomyces cerevisiae AH 22/pAT 77) has been deposited at Fermentation Research Institute, Agency of Industrial Science and Technology, Japan under Budapest Treaty as "FERM BP-324".

The pAT 77 thus obtained (1 μg) is cleaved with Sal I and then is treated with an exonuclease BAL 31 (0.1 U) in a solution (50 μl) of 20 mM Tris-HCl (pH 8.2), 12 mM $CaCl_2$, 12 mM $MgCl_2$, 0.2M NaCl and 1 mM EDTA for 30 seconds to one minute. The reaction mixture is subjected to phenol extraction and ethanol precipitation in the same manner as described in Preparation (1) (ii) (A) hereinafter. The resulting precipitates are treated with Xho I linker (1 pmol) and T4 DNA ligase under the same conditions as described in Preparation (1) (ii) (A) hereinafter for 12 hours.

E. coli χ1776 is treated with the above reaction mixture by the procedure as described in R. III. Curtiss et al, "Molecular cloning of recombinant DNA" eds. W. A. Scott and R. Werner, page 99, Academic Press (1977) so as to transform the E. coli χ1776 to give an ampicillin-resistant transformant. From the resulting transformant colonies, plasmid DNAs are prepared by the procedure as described by K. Matsubara (j. Virol., 16, 479, 1975). According to Maxam-Gilbert method (cf. Maxam, A. & Gilbert, W.; Pro. N.A.S., 74, 560–564), the nucleotide sequence of the resulting DNAs is determined, and further, the region of the acid phosphatase gene deleted with BAL 31 is determined. Among these DNAs, the desired plasmids pAM 81, pAM 82, pAM 83 and pAM 84 which are completely deficient in whole of the structural gene of phosphatase are selected and isolated.

Designating "A" in the codon ATG encoding the first amino acid (methionine) of the product P60 of the phosphatase structural gene as "+1", the following regions are deleted in these shuttle vectors, pAM 81: till +2, pAM 82: till −33, pAM 83: till −50, and pAM 84: till −51. The pAM 81, pAM 82, pAM 83 and pAM 84 carried on *Saccharomyces cerevisiae* (i.e. *Saccharomyces cerevisiae* AH 22/pAM 81, AH 22/pAM 82, AH 22/pAM 83 and AH 22/pAM 84, respectively) have been deposited at Fermentation Research Institute, Agency of Industrial Science and Technology, Japan under Budapest Treaty as "FERM BP-325", "FERM BP-313", "FERM BP-327", and "FERM BP-326", respectively.

An enbodiment of preparation of recombinant plasmid, transformed yeast therefrom and HBsAg by recombination of HBV DNA using the shuttle vector pAM 82 is illustrated in the following Preparation.

Preparation (1) Preparation of HBV DNA (i) Preparation of virus DNA

A pooled blood plasma (700 ml) obtained from ten persons who are positive in HBsAg (subtype adr) and HBeAg is centrifuged at 5,000 r.p.m. for 20 minutes to remove undissolved materials. The resulting solution is centrifuged at 4° C., 18,000 r.p.m. for 8 hours, and the resultant precipitates are re-dissolved in 10 ml of a buffer (pH 7.5) of 10mM Tris-HCl, 0.1M NaCl and 1 mM EDTA. The solution is added to the top of a centrifugal tube containing 30% sucrose, which is centrifuged at 4° C., 39,000 r.p.m. for 4 hours. The resultant precipitates are re-dissolved in the same buffer as above.

In order to make easier the following operation, the buffer solution is subjected to the reaction by HBV DNA polymerase by treating it in a mixture (500 µl) of 67 mM Tris-HCl (pH 7.5), 80 mM NH$_4$Cl, 25 mM MgCl$_2$, 0.5% NP40 (tergitol, manufactured by Sigma Co.), 0.1% 2-mercaptoethanol, 330 µM dCTP (deoxycytidine triphosphate), dGTP (deoxyguanosine triphosphate), and dATP (deoxyadenosine triphosphate), 0.5 µM α-[$^{32}$P]dTTP (deoxythymidine triphosphate) at 37° C. for 3 hours, and to the reaction mixture is added the same volume of 100 mM EDTA solution. By the above DNA polymerase reaction, single-stranded region of the DNA is repaired to wholly double-strand to give a [$^{32}$P] labeled material. This material is added to the top of a centrifugal tube wherein 30%, 20% and 10% aqueous solutions of sucrose are packed in layers in this order, and it is centrifuged at 4° C. 39,000 r.p.m. for 4.5 hours.

In order to digest the proteins strongly bonded to DNA, the precipitates obtained above are treated in a mixture (200 µl) of 1 mg/ml of pronase E (manufactured by Kaken Kagaku K.K.) and 0.2% aqueous sodium lauryl sulfate solution at 37° C. for 2 hours. The resulting mixture is extracted with phenol (200 µl) twice, and the resulting DNA-containing extract is washed with ether to remove phenol solvent to give a solution of HBV DNA. The DNA thus obtained has a specific radioactivity of 2.5×10$^6$ cpm/µg and can be used for digestion with restriction enzymes.

(ii) Cloning of HBV DNA

The double-stranded circular HBV DNA obtained above is cloned by using λ-phage Sharon 16A DNA as a vector and then is again cloned by using the known plasmid pACYC177 as a vector as follows.

(A) Cloning in the system of λ-phage Sharon 16A host-vector:

HBV DNA (20 ng) is treated with endonuclease Xho I in a mixture (20 µl) of 10 mM Tris-HCl (pH 7.4), 7 mM MgCl$_2$, 100 mM NaCl and 7 mM 2-mercaptoethanol at 37° C. for 2 hours. The resulting mixture is extracted with phenol (20 µl) and further with ether, and to the aqueous layer is added a double volume of cooled ethanol to precipitate DNA. The mixture is kept at −70° C. for one hour and then centrifuged at 10,000 r.p.m. for 5 minutes, and the precipitated DNA is recovered. The precipitates thus separated are dissolved in a mixture (5µl) of 10 mM Tris-HCl (pH 7.4) and 1 mM EDTA. The HBV DNA and an equimolar amount of λ-phage Sharon 16 A DNA (having one recognition site of Xho I) obtained by cleavage with endonuclease Xho I in the same manner as above are reacted with T4 DNA ligase [a mixture of 50 mM Tris-HCl (pH 7.4), 10 mM MgCl$_2$, 10 mM dithiothreitol, 100 µg/ml calf serum albumin, 0.5 mM ATP and 0.5 µl enzyme preparation (T4 ligase, manufactured by Takara biomedicals, 1–5×10$^3$ unit/ml)] at 4° C. for 18 hours. The reaction mixture is extracted with phenol and ether and then subjected to precipitation with ethanol in the same manner as described above. The precipitates thus obtained are dissolved in a mixture (10 µl) of 10 mM Tris-HCl (pH 7.4) and 1 mM EDTA.

The thus annealed DNA is subjected to in vitro packaging operation to form λ-phage in the same manner as described in "Methods in Enzymology", 68, 299–309 and further plaques (10$^4$) are formed therefrom on an L-agar plate (23 cm×23 cm) by using *E. coli* DP50 SupF (cf. Blattner, F. R. et al, Science 196, 161, 1977) as an indicator. These plaques are subjected to plaque hybridization using $^{32}$P-labeled HBV DNA prepared above as a probe (cf. Science, 196, 180, 1977) in order to select plaques formed from the phage having HBV DNA, by which a plural of the desired phages are separated.

(B) Re-cloning by using plasmid pACYC177 as a vector:

From the phage having HBV DNA obtained in the above (A), a phage DNA is prepared by using *E. coli* DP50-SupF as a bacteria to be infected in the same manner as described in "Methods in Enzymology", 68, 245–378, 1979. The DNA thus obtained is digested with Xho I under the same conditions as described above for 2 hours, and the resulting reaction mixture is subjected to an electrophoresis with 0.75% agarose gel to isolate HBV DNA (3.2 kb). The HBV DNA is absorbed onto DEAE (diethylaminoethyl cellulose) paper (manufactured by Toyo Roshi, Japan) in order to separate from the vector DNA and then eluted with 1M NaCl aqueous solution to give an HBV DNA having Xho I terminals at both ends.

Separately, plasmid pACYC177 (cf. Chang, A. C. Y., Cohen, S. N.; J. Bacteriol., 134, 1141–1156, 1978) having a single Xho I cleavage site within kanamycin-resistant gene thereof is digested with Xho I, and the product is purified by phenol extraction, ether treatment and ethanol precipitation in the same manner as described above.

The thus obtained pACYC177 cleaved with Xho I is mixed with XhoI-terminal HBV DNA obtained above in a molar ratio of 1:5, and the mixture is annealed with T4 DNA ligase for 18 hours as described above.

The annealed DNA preparation (10 μl) obtained above is added to a liquid of *E. coli* (0.1 ml) which is prepared by treating a culture broth of *E. coli* χ1776 [cf. R. III. Curtiss, et al, "Molecular cloning of recombinant DNA" eds. W. A. Scott and R. Werner, page 99, Academic Press (1977)] by the procedure as described in M. V. Norgard, Gene, 3, 279 (1978), and the mixture is mixed well and allowed to stand at 0° C. for 25 minutes. The mixture is applied onto an L-agar plate containing ampicillin (20 μg/ml), α-biotine (1 μg/ml), diaminopimelic acid (100 μg/ml) and thymine (20 μg/ml) and is incubated at 37° C. overnight. The resulting colonies are applied onto both an agar plate containing kanamycin (20 μg/ml) and an agar plate containing ampicillin (20 μg/ml), and the colonies which grow only on the agar plate containing ampicillin is selected. pACYC177 has an ampicillin-resistant gene and a kanamycin-resistant gene, but when it is inserted with HBV DNA at the Xho I site of the kanamycin-resistant gene, it looses the kanamycin-resistance. Accordingly, the selected colonies have a recombinant DNA of pACYC177-HBV DNA. From the colonies thus selected, a plasmid is prepared by the procedure as described by K. Matsubara (J. Virol., 16, 479, 1975). The plasmid thus obtained, i.e. the recombinant DNA of pACYC177-HBV DNA (which is designated "pHBV"), is treated with Xho I under the same conditions as described above to give total HBV DNA fragment (3.2 kb). Besides, when it is treated with Xho I and BamHI, there is obtained a fragment (about 1.3 kb) containing an HBsAg gene.

(2) Preparation of HBsAg gene-expression plasmids (i) Preparation of plasmids inserted with whole of HBV DNA HBV DNA obtained by treating a plasmid pHBV (pACYC 177-HBV DNA) with Xho I is recombined with Xho I cleaved shuttle vector, pAM 82 in the molar ratio of 5:1 by annealing with T4 DNA ligase under the same conditions as described above.

*E. coli* χ1776 is transformed with the reaction mixture and a plasmid DNA is prepared from the resulting ampicillin-resistant transformant in the same manner as described hereinbefore. The DNAs thus prepared are analyzed with various restriction enzymes, such as Xho I, Xba I and Hind III, and thereby, insertion of HBV DNA into the vectors and direction thereof are determined.

The thus obtained HBsAg gene-expression plasmids have HBs gene and HBc gene in this order downstream the phosphatase promoter, and the plasmids is designated pAH 203.

(ii) Preparation of plasmid inserted with HBsAg gene fragment

An HBsAg gene fragment (3 μg) prepared by cleaving plasmid pHBV with BamHI is treated with T4 DNA polymerase (0.2 U) in a solution (100 μl) of 67 mM Tris-HCl (pH 8.6), 6.7 mM $MgCl_2$, 10 mM 2-mercaptoethanol, 6.7 μM EDTA and 16.7 mM $(NH_4)_2SO_4$ which contains 200 μM αATP, αCTP, αTTP and αGTP for 30 minutes in order to fill-in the BamHI cleavage end. The reaction mixture is subjected to phenol extraction and ethanol precipitation as described above. The resulting precipitates are subjected to linking reaction with Xho I linker in a molar ratio of 1:10 with T4 DNA ligase under the same conditions as described hereinbefore. After phenol extraction and ethanol precipitation, the resulting plasmid is treated with Xho I to give an HBsAg gene fragment (about 1.3 kb) having Xho I cleavage terminal at both ends. The fragment thus obtained is annealed with the shuttle vector pAM 82 which is cleaved with Xho I in a molar ratio of 5:1 by using T4 DNA ligase, and *E. coli* χ776 is transformed with the reaction mixture obtained above in the same manner as described in the above (1) (ii) (B) to give a plasmid DNA.

The plasmid thus obtained is inserted with HBsAg gene in a correct direction downstream the phosphatase promoter of the vector pAM 82, which plasmid is designated pAS 101.

(3) Preparation of transformed yeast

The starting yeast is *Saccharomyces cerevisiae* AH22 [a, leu2, his4, can1 (Cir⁺)], which has been deposited at Fermentation Research Institute, Agency of Industrial Science and Technology, Japan under Budapest Treaty as "FERM BP-312". The starting yeast is inoculated in YPD medium (100 ml) consisting of 2% polypeptone, 1% yeast extract and 2% glucose, and the mixture is incubated at 30° C. overnight, and thereafter, the cells are collected by centrifugation. The cells thus collected are washed with sterilized water (20 ml), suspended in a solution (5 ml) of 1.2M sorbitol and 100 μg/ml zymolyase-60,000 (manufactured by Seikagaku Kogyo K.K., Japan), and the suspension is allowed to stand at 30° C. for 30 minutes to give spheroplast. The spheroplast thus prepared is washed with 1.2M sorbitol solution three times, and then suspended in a solution (0.6 ml) of 2M sorbitol, 10 mM $CaCl_2$ and 10 mM Tris-HCl (pH 7.5). The suspension thus prepared is divided into a small test tube in a volume of 60 μl. To the suspension is added the solution of the recombinant plasmid pAH 203 (30 μl) prepared in the above (3). After mixing well, 0.1M $CaCl_2$ (3 μl) is added thereto in a final concentration of 10 mM $CaCl_2$, and the mixture is allowed to stand at room temperature for 5 to 10 minutes. To the resulting mixture is added each 1 ml of a solution of 20% polyethylene glycol 4,000, 10 mM $CaCl_2$ and 10 mM Tris-HCl (pH 7.5), and the mixture is allowed to stand at room temperature for about 20 minutes. The resulting mixture (each 0.2 ml) is added to a medium (10 ml) consisting of 22% sorbitol, 2% glucose, 0.7% yeast nitrogen base amino acid, 2% YPD, 20 μg/ml histidine and 3% agar, which is kept at a constant temperature of 45° C. After gentle mixing, the mixture is added in a layer onto a plate of minimal medium containing 1.2M sorbitol which is previously prepared and consists of 0.7% yeast nitrogen base amino acid, 2% glucose, 20 μg/ml histidine and 2% agar and is set thereon. The plate is incubated at 30° C. to give a colony of a leucine-non-requiring yeast. The colony is incubated in a BurkHolder minimal medium supplemented with histidine (20 μg/ml) [cf. Tohe, A, et al; J. Bachterol., 113, 727–738, 1973] to give the desired transformed yeast: *Saccharomyces cerevisiae* pAH 203.

In the same manner as described above, except that the recombinant plasmid PAS 101 is used instead of the recombinant pAH 203, *Saccharomyces cerevisiae* pAS 101 is prepared.

(4) Production of HBsAg with the transformed yeast

Each colony of the transformed yeasts obtained in the above (3) is applied onto an agar plate of BurkHolder minimal medium supplemented with histidine (20 μg/ml) and incubated at 30° C. to form a colony (in order to confirm the transformant requiring no leucine). The resulting cells are separated from the colony, inoculated into BurkHolder minimal medium supplemented with histidine (20 μg/ml) and incubated at 30° C. After about 24 hours, the cells in logarithmic growth phase are collected by centifugation, suspended in a minimal medium (10 ml) containing no phosphoric acid (which is prepared by replacing $KH_2PO_4$ in BurkHolder minimal medium with KCl, followed by supplementing with 20 μg/ml histidine) in a cell concentration of about $4 \times 10^6$ cells/ml. After incubating at 30° C. for about 24 hours, the culture broth is centrifuged at 4,000 r.p.m. for 10 minutes to collect the cells. The cells thus separated are suspended in a solution (3 ml) of 1.2M sorbitol, 50 mM phosphate buffer (pH 7.2), 14 mM 2-mercaptoethanol and 100 µg/ml Zymolyase-60,000 (manufactured by Seikagaku Kogyo K.K., Japan), and the mixture is gently shaken at 30° C. for 30 minutes to give spheroplast. The spheroplast is collected by centrifugation and is well suspended in a solution (1 ml) of 0.1% tritone X-100 and 50 mM phosphate buffer (pH 7.2), stirred vigorously and then centrifuged at 7,000 r.p.m. for 10 minutes, and the resulting supernatant is taken as the yeast-lysed solution.

The lysed solution (20 µl) obtained above is tested with HBs antigen RIA kit (manufactured by Abbott, U.S.A.) in terms of the HBs antigen activity. The results are shown in Table 1.

TABLE 1

| Clone No. | Host | Plasmid | HBsAg activity (cpm) |
|---|---|---|---|
| 1 | S. Cerevisiae AH22 (FERM BP-312) | pAH 203 | 13,008 |
| 2 | S. Cerevisiae AH22 (FERM BP-312) | pAS 101 | 11,200 |
| Reference | S. Cerevisiae AH22 (FERM BP-312) | pAM 82* | 320 |

*) This vector has no HBV or HBs gene and is used as a negative reference. (The negative control of RIA kit has an activity of 310 cpm, and the positive control thereof has that of 17,500 cpm)

(5) Preparation of HBcAg gene expression plasmid

An HBcAg gene fragment is prepared by the following procedure.

Plasmid pHBV (3 µg) is digested with restriction endonuclease Rsa I in a usual manner. The reaction mixture is subjected to phenol extraction and ethanol precipitation as described above. The resulting precipitates are subjected to linking reaction with Xho I linker in a molar ratio of 1:10 with T4 DNA ligase. After phenol extraction and ethanol precipitation, the resulting precipitates are subjected to Xho I digestion to give an HBc gene fragment (about 0.7 kb) having Xho I cleavage terminal at both ends.

The fragment thus obtained is annealed with the shuttle vector pAM 82 which is cleaved with Xho I in a molar ratio of 5:1 by using T4 DNA ligase. The raction mixture is used to transform E. coli χ1776 in the same manner as described in (1) (ii) (B) to give a plasmid DNA. The plasmid thus obtained is inserted with HBcAg gene in a correct direction downstream the phosphatase promoter of the vector pAM 82, which plasmid is designated pHC 301.

(6) Preparation of transformed yeast with HBcAg gene expression plasmid pHC 301

The starting yeast is Saccharomyces cerevisiae AH22 [a leu2 his4 can1 (Cir⁺)], which has been deposited at Fermentation Research Institute, Agency of Industrial Science and Technology, Japan under Budapest Treaty as "FERM BP-312". The starting yeast is inoculated in YPD medium (100 ml) consisting of 2% polypeptone, 1% yeast extract and 2% glucose, and the mixture is incubated at 30° C. overnight, and thereafter, the cells are collected by centrifugation. The cells thus collected are washed with sterilized water (20 ml), suspended in a solution (5 ml) of 1.2M sorbitol and 100µg/ml zymolyase-60,000 (manufactured by Seikagaku Kogyo K.K., Japan), and the suspension is allowed to stand at 30° C. for 30 minutes to give spheroplast. The spheroplast thus prepared is washed with 1.2M sorbitol solution three times, and then suspended in a solution (0.6 ml) of 2M sorbitol, 10 mM $CaCl_2$ and 10 mM Tris-HCl (pH 7.5). The suspension thus prepared is divided into a small test tube in a volume of 60 µl. To the suspension is added the solution of the recombinant plasmid pAC 301 (30 µl) prepared in the above (5). After mixing well, 0.1M $CaCl_2$ (3 µl) is added thereto in a final concentration of 10 mM $CaCl_2$, and the mixture is allowed to stand at room temperature for 5 to 10 minutes. To the resulting mixture is added each 1 ml of a solution of 20% polyethylene glycol 4,000, 10 mM $CaCl_2$ and 10 mM Tris-HCl (pH 7.5), and the mixture is allowed to stand at room temperature for about 20 minutes. The resulting mixture (each 0.2 ml) is added to a medium (10 ml) consisting of 22% sorbitol, 2% glucose, 0.7% yeast nitrogen base amino acid, 2% YPD, 20 µg/ml histidine and 3% agar, which is kept at a constant temperature of 45° C. After mixing mildly, the mixture is added in a layer onto a plate of minimal medium containing 1.2M sorbitol which is previously prepared and consists of 0.7% yeast nitrogen base amino acid, 2% glucose, 20 µg/ml histidine and 2% agar and is set thereon. The mixture is incubated at 30° C. to give colonies of leucine-non-requiring yeast. The colony is incubated in a BurkHolder minimal medium supplemented with histidine (20 µg/ml) [cf. Tohe, A, et al; J. Bachterol., 113, 727–738, 1973] to give the desired transformed yeast: Saccharomyces cerevisiae pHC 301.

(7) Production of HBcAg with the transformed yeast

Each colony of the transformed yeasts obtained in the above (6) is applied onto an agar plate of BurkHolder minimal medium supplemented with histidine (20 µg/ml) and incubated at 30° C. to form a colony (in order to confirm the transformant requiring no leucine). The resulting cells are separated from the colony, inoculated into BurkHolder minimal medium supplemented with histidine (20 µg/ml) and incubated at 30° C. After about 24 hours, the cells in logarithmic growth phase are collected by centifugation, suspended in a minimal medium (10 ml) containing no phosphoric acid (which is prepared by replacing $KH_2PO_4$ in BurkHolder minimal medium with KCl, followed by supplementing with 20 µg/ml histidine) in a cell concentration of about $4 \times 10^6$ cells/ml. After incubating at 30° C. for about 24 hours, the culture broth is centrifuged at 4,000 r.p.m. for 10 minutes to collect the cells. The cells thus separated are suspended in a solution (3 ml) of 1.2M sorbitol, 50 mM phosphate buffer (pH 7.2), 14 mM 2-mercaptoethanol and 100 µg/ml Zymolyase-60,000 (manufactured by Seikagaku Kogyo K.K., Japan), and the mixture is gently shaken at 30° C. for 30 minutes to give spheroplast. The spheroplast is collected by centrifugation and is well suspended in a solution (1 ml) of 0.1% tritone X-100 and 50 mM phosphate buffer (pH 7.2), stirred vigorously and then centrifuged at 7,000 r.p.m. for 10 minutes, and the resulting supernatant is taken as the yeast-lysed solution.

The lysed solution (20 µl) obtained above is tested with HBc antigen RIA kit (manufactured by Abbott, U.S.A.) in terms of the HBc antigen activity. The results are shown in Table 2.

TABLE 2

| | Host | Plasmid | HBsAg activity (cpm) |
|---|---|---|---|
| | S. Cerevisiae AH22 (FERM BP-312) | pHC 301 | 4,989 |
| Reference | S. Cerevisiae AH22 (FERM BP-312) | pAM 82* | 16,913 |

*) This vector has no HBV or HBs gene and is used as a negative reference. (The negative control of RIA kit has an activity of 17,740 cpm, and the positive control thereof has that of 446 cpm)

What is claimed is:
1. The shuttle vector designated pAM 82.

* * * * *

UNITED STATES PATENT AND TRADEMARK OFFICE
CERTIFICATE OF CORRECTION

PATENT NO. : 5,707,862
DATED : January 13, 1998
INVENTOR(S) : Atsushi MIYANOHARA et al.

It is certified that error appears in the above-identified patent and that said Letters Patent is hereby corrected as shown below:

Title page; Column 1, item [22], contains an error wherein "December 5, 1990" should read --November 29, 1990--; and item [63] Continuation of Ser. No. "61,441, Jun. 15, 1987" should read --61,440, Jun. 15, 1987--.

Signed and Sealed this

Twenty-fifth Day of August, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,707,862
DATED : January 13, 1998
INVENTOR(S) : Atsushi MIYANOHARA et al.

It is certified that error appears in the above-identified patent and that said Letters Patent is hereby corrected as shown below:

On the title page item,

[30]    Foreign Aplication Priority Data add:

--August 20, 1982   [JP]    145093/1982--

Signed and Sealed this

Eighth Day of December, 1998

Attest:

BRUCE LEHMAN

*Attesting Officer*    *Commissioner of Patents and Trademarks*